United States Patent
Uchiyama et al.

(10) Patent No.: US 8,101,124 B2
(45) Date of Patent: Jan. 24, 2012

(54) METHOD OF FRESHENING AIR

(75) Inventors: Hirotaka Uchiyama, Loveland, OH (US); Christopher Eugene Bates, Cincinnati, OH (US); Eric Laurence Wagnon, Cincinnati, OH (US); Cynthia Jean McCann, Cincinnati, OH (US); Carl-Eric Kaiser, Mason, OH (US); Steven Louis Diersing, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/175,164

(22) Filed: Jul. 1, 2011

(65) Prior Publication Data

US 2011/0318222 A1    Dec. 29, 2011

Related U.S. Application Data

(63) Continuation of application No. 10/881,173, filed on Jun. 30, 2004, now Pat. No. 7,998,403.

(51) Int. Cl.
*A61L 9/00* (2006.01)
*A62B 7/08* (2006.01)
*B67B 7/00* (2006.01)
*G01F 11/00* (2006.01)

(52) U.S. Cl. .............. 422/5; 422/120; 422/123; 222/1

(58) Field of Classification Search .............. 422/5, 120, 422/123; 222/1
See application file for complete search history.

(56) References Cited

U.S. PATENT DOCUMENTS

| | | | |
|---|---|---|---|
| 3,583,642 A | 6/1971 | Crowell et al. |
| 3,828,104 A | 8/1974 | Barnhurst et al. |
| 5,143,288 A | 9/1992 | Kohler et al. |
| 5,143,900 A | 9/1992 | Steltenkamp et al. |
| 5,578,563 A | 11/1996 | Trinh et al. |
| 5,593,670 A | 1/1997 | Trinh et al. |
| 5,891,427 A | 4/1999 | Mettler |
| 5,942,217 A | 8/1999 | Woo et al. |
| 5,955,093 A | 9/1999 | Woo et al. |
| 6,033,679 A | 3/2000 | Woo et al. |
| 6,248,135 B1 | 6/2001 | Trinh et al. |

(Continued)

FOREIGN PATENT DOCUMENTS

AU    632263 B2    10/1992

(Continued)

OTHER PUBLICATIONS

PCT International Search Report, Mailed Oct. 5, 2005, 4 Pages.

*Primary Examiner* — Sean E Conley
*Assistant Examiner* — Regina M. Yoo
(74) *Attorney, Agent, or Firm* — Amy I Ahn-Roll; Leonard W Lewis

(57) ABSTRACT

Air freshener products and methods for freshening air are disclosed. In some embodiments, the air freshening product may include a container for storing an air freshening composition that may contain compressed gas such as compressed air, nitrogen, nitrous oxide, inert gases, or carbon dioxide. When the container is completely filled with propellant and air freshening composition, the air freshening composition may be released from the container at a flow rate of from about 0.8 grams/second to about 1.5 grams/second, wherein the mean particle size of the released spray droplets is from about 10 microns to about 100 microns.

The method of freshening air, in certain embodiments, provides improved delivery of an air freshening composition using a non-hydrocarbon propellant. If malodor counteractants are used, the method may also provide a reduction in malodors.

13 Claims, 9 Drawing Sheets

U.S. PATENT DOCUMENTS

| | | |
|---|---|---|
| 6,279,834 B1 | 8/2001 | Fox et al. |
| 6,284,231 B1 | 9/2001 | Trinh et al. |
| 6,287,550 B1 | 9/2001 | Trinh et al. |
| 6,415,992 B1 | 7/2002 | Blondeel et al. |
| 6,592,813 B1 | 7/2003 | Fox et al. |
| 7,014,127 B2 | 3/2006 | Valpey et al. |
| 2001/0013352 A1 | 8/2001 | Poisson et al. |
| 2002/0032147 A1 | 3/2002 | Foley et al. |
| 2003/0150885 A1 | 8/2003 | Dunne |
| 2004/0144864 A1 | 7/2004 | Valpey et al. |
| 2004/0223871 A1 | 11/2004 | Woo et al. |
| 2004/0223943 A1 | 11/2004 | Woo et al. |
| 2007/0172382 A1 | 7/2007 | Uchiyama et al. |

FOREIGN PATENT DOCUMENTS

| | | |
|---|---|---|
| GB | 1012413 A | 12/1965 |
| JP | 2002309242 A | 10/2002 |
| JP | 2002369873 A | 12/2002 |
| KR | 2001-0013619 | 2/2001 |

Figure 1: Aerosol Perfume Profile Map

Figure 6: Mass Spectrum of Lilial

METHOD OF FRESHENING AIR

CROSS REFERENCE TO RELATED APPLICATIONS

This application is a Continuation of U.S. application Ser. No. 10/881,173, filed on Jun. 30, 2004 now U.S. Pat. No. 7,998,403, which in turn claims the benefit of U.S. patent application Ser. No. 10/429,593, filed on May 5, 2003.

FIELD OF THE INVENTION

The present invention relates to air fresheners and methods for freshening air.

BACKGROUND OF THE INVENTION

Products for reducing or masking malodors in the air are currently available, and are described in the patent literature. Products for reducing or masking malodors on fabrics and other surfaces are also currently available and described in the patent literature.

S.C. Johnson sells products such as GLADE® sprays and the OUST™ fabric refresher.

Reckitt-Benckiser sells products such as LYSOL® disinfectant sprays, AIR WICK® by WIZARD® products.

Some of these products use hydrocarbons as propellants. Products that use hydrocarbons as propellants can be subject to the disadvantage that any scent or perfume used therein tends to evaporate very quickly due to the small size of the droplets that are dispensed with hydrocarbon propellants and the rapid phase change of hydrocarbon propellants from liquid to gas. In the case of air fresheners, this can result in a less desirable consumer experience of an overwhelming burst of perfume initially and a short longevity period during which these perfumes can be detected in the air. In order to attempt to increase the period during which these perfumes can be detected, the tendency is to put additional perfume into products that utilize hydrocarbons as propellants. This may result in a perfume level that initially has a tendency to be too strong, or overpowering, yet may still not be long lasting.

Some of these products may cause fabrics to turn yellow or brown under natural light, particularly products that contain certain types of aldehydes.

The Procter & Gamble Company sells products under the FEBREZE® fabric refresher brand name. These products typically contain cyclodextrin and do not use propellants. Procter & Gamble patents include U.S. Pat. No. 5,942,217, U.S. Pat. No. 5,955,093, U.S. Pat. No. 6,033,679.

SUMMARY OF THE INVENTION

The present invention relates to air fresheners, or air freshening products, and methods for freshening air. The air freshening product may comprise a container for storing an air freshening composition that may contain a perfume composition or may contain a perfume composition in conjunction with a malodor counteractant, and the container may comprise a propellant such as a compressed gas, and a dispenser. There are numerous embodiments of the products described herein, all of which are intended to be non-limiting examples.

In some non-limiting embodiments, the air freshening product may include a container for storing an air freshening composition that may contain non-hydrocarbon compressed gas such as compressed air, nitrogen, nitrous oxide, inert gases, or carbon dioxide. When the container is completely filled with propellant and air freshening composition, the air freshening composition may be released from the container at a flow rate of from about 0.8 grams/second to about 1.5 grams/second, wherein the mean particle size of the released spray droplets is from about 10 microns to about 100 microns. The method of freshening air, in certain embodiments, provides improved delivery of an air freshening composition using a non-hydrocarbon propellant. If malodor counteractants are used, the method may also provide a reduction in malodors.

In other non-limiting embodiments, the air freshening product delivers a consistent perfume release profile. In these, or other embodiments, the air freshening product may also deliver a genuine malodor removal benefit without impacting the character of the parent fragrance (that is, the perfume composition without any malodor counteractants). A "consistent perfume release profile" is defined as a perceivable perfume intensity which is delivered initially and a comparable intensity is maintained for at least 10 minutes or longer (e.g., 30 minutes, or more). A "genuine malodor removal benefit" is defined as an analytically measurable malodor reduction. Thus, if the air freshening product delivers a genuine malodor removal benefit, the air freshening product will not function merely by using perfume to cover up or mask odors. The air freshening product may be fabric-safe so that it does not stain fabrics with which it comes into contact. Furthermore, in some versions of this embodiment, the product may also be suitable for use as a fabric refresher.

The air freshening product can be sprayed into the air. Any suitable type of article can be used to spray the air freshening product into the air. The air freshening product can be sprayed using any suitable type of sprayer. One suitable type of sprayer is an aerosol sprayer. If an aerosol sprayer is used, it can use any suitable type of propellant. The propellant can include hydrocarbon propellants, or non-hydrocarbon propellants. In some embodiments, it is desirable to use propellants that are primarily non-hydrocarbon propellants (that is, propellants that are comprised of more non-hydrocarbon propellants by volume than hydrocarbon propellants, that is, greater than (or equal to) about 50% of the volume of the propellant). In some embodiments, the propellant may be substantially free of hydrocarbons. In embodiments in which the air freshener uses a non-hydrocarbon propellant, such a propellant may include, but is not limited to a compressed gas. Suitable compressed gases include, but are not limited to compressed air, nitrogen, nitrous oxide, inert gases, carbon dioxide, etc.

In one version of such an embodiment, at least some of the spray droplets are sufficiently small in size to be suspended in the air for at least about 10 minutes, and in some cases, for at least about 15 minutes, or at least about 30 minutes. The spray droplets can be of any suitable size. In some embodiments, at least some of the spray droplets have a diameter in a range of from about 0.01 μm to about 500 μm, or from about 5 μm to about 400 μm, or from about 10 μm to about 200 μm. The mean particle size of the spray droplets may be in the range of from about 10 μm to about 100 μm, or from about 20 μm-about 60 μm.

In some embodiments, the air freshener product comprises a perfume that is formulated so that it has an initial impact that is not overpowering and is perceived in the air for a longer period of time. Without wishing to be bound to any particular theory, it is believed that the perfume longevity may be attributed to using a compressed gas, such as nitrogen as a propellant combined with a larger droplet size (relative to some aerosol spayers). Again, without wishing to be bound to any particular theory, such larger droplets may act as reservoirs for the perfume that provide a source of olfactive molecules, and which continue to emit molecules providing a continual source of fragrance in the room. It is believed that smaller molecules will provide droplets with a greater total surface area that causes the perfume to more quickly release from the same. In some embodiments, the perfume remains in the air for at least about 10 minutes, or more, up to about 30 minutes, or more (or any period therebetween), while maintaining substantially the same character.

The air freshening product can be packaged in any suitable container. Suitable containers include aerosol cans. In one embodiment, the aerosol can may have a dispenser that sprays the air freshening composition at an angle that is between an angle that is parallel to the base of the container and an angle that is perpendicular thereto. In other embodiments, the desired size of spray droplets can be delivered by other types of devices that are capable of being set to provide a narrow range of droplet size. Such other devices include, but are not limited to: foggers, ultrasonic nebulizers, electrostatic sprayers, and spinning disk sprayers.

BRIEF DESCRIPTION OF THE DRAWINGS

While the specification concludes with claims particularly pointing out and distinctly claiming the invention, it is believed that the present invention will be better understood from the following description taken in conjunction with the accompanying drawings in which:

DETAILED DESCRIPTION OF THE INVENTION

The present invention relates to air fresheners or air freshening products and methods for freshening air. The air freshening product may comprise a container for storing an air freshening composition, and the container may comprise a propellant such as a compressed gas, and a dispenser; and an air freshening composition. There are numerous embodiments of the air freshening products and methods described herein, all of which are intended to be non-limiting examples.

The Air Freshening Composition

The term "air freshening composition", as used herein, refers to any suitable composition that reduces odors in air, and/or reduces the impression of odors in the air by masking, layering or including malodor counteractant perfume raw materials into the composition. Numerous types of air freshening compositions are possible.

In certain embodiments, the air freshening composition comprises a perfume composition. In some embodiments, the air freshening product delivers a consistent perfume release profile without an overwhelming initial burst of perfume. A "consistent perfume release profile" is defined as a perceivable perfume intensity which is delivered initially and a comparable level of intensity is maintained for at least 10 minutes or longer, and in some cases, for at least about 15 minutes, at least about 20 minutes, at least about 25 minutes, or at least about 30 minutes. The intensities at these times may be respectively referred to as the "ten minute intensity", the "fifteen minute intensity", etc.

Figure 1:
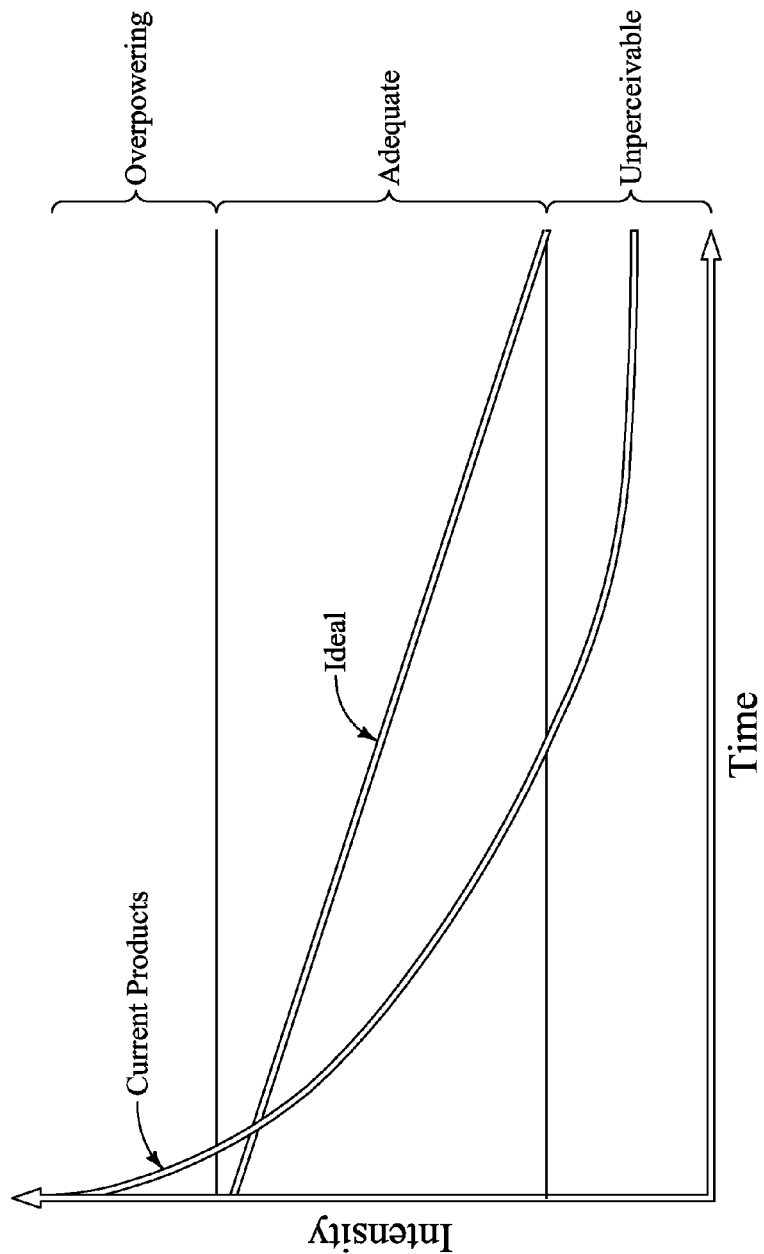
FIG. 1 is a graph that compares the perfume release profile of an example of an air freshener having a high initial perfume intensity, and a relatively short period of longevity in the air to an example of an air freshener having a more consistent perfume release profile, and longer period of longevity in the air.

FIG. 1 is a graph that compares the perfume release profile of an example of an air freshener having a high initial perfume intensity, and a relatively short period of longevity in the air to an example of an ideal air freshener having a more consistent perfume release profile, and longer period of longevity in the air.

Figure 2:
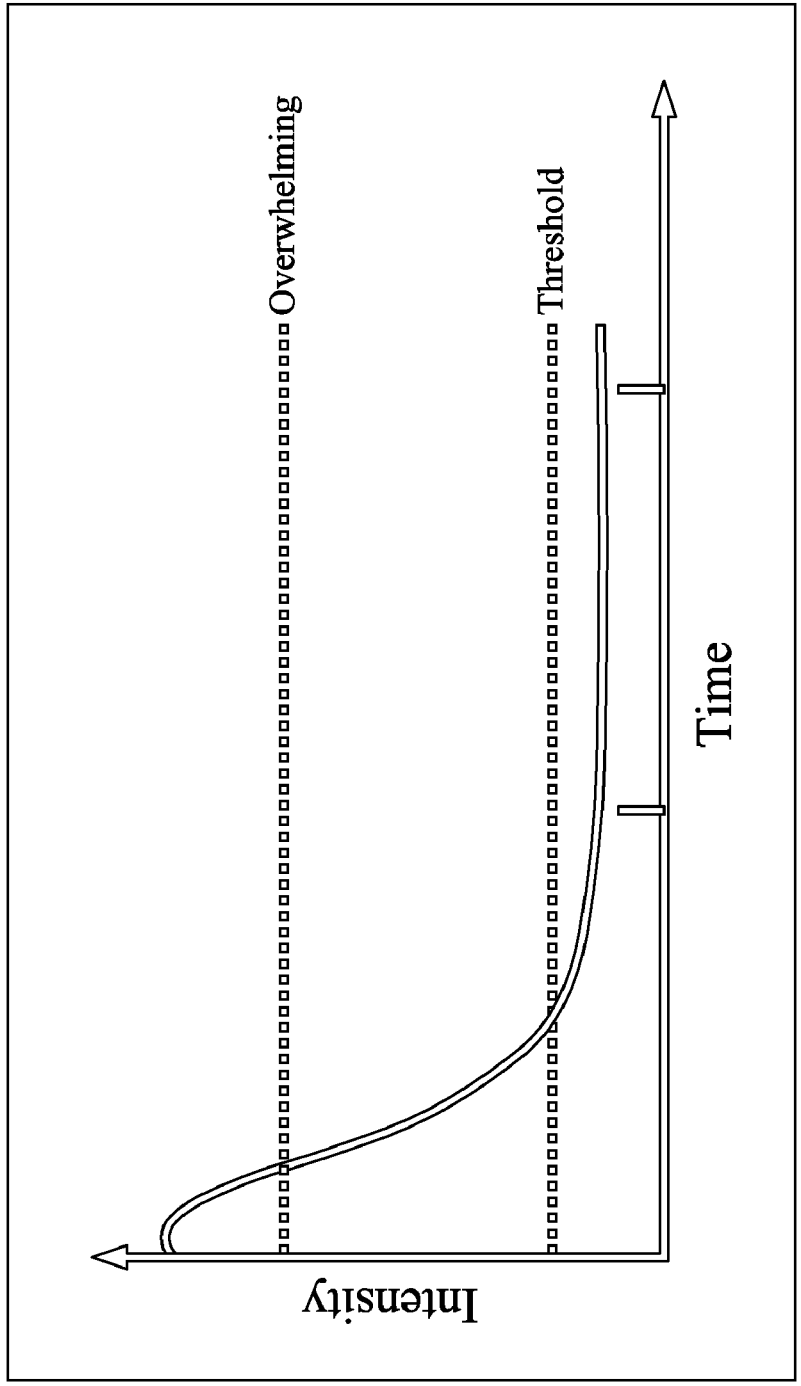
FIG. 2 is a graph that shows the perfume release profile with respect to the odor detection threshold of an example of an air freshener having a high initial perfume intensity, and a relatively short period of longevity in the air.

FIG. 2 is a graph of the perfume release profile of an example of an air freshener having an initial high perfume intensity, and a relatively short period of longevity in the air. As shown in FIG. 2, the initial intensity of the perfume in the air is quite high, and can contribute to consumers experiencing an overwhelming initial burst of perfume. Following the initial burst of perfume, FIG. 2 shows that the intensity of the perfume in the air quickly drops off, and falls below the detection threshold of an untrained person's sense of smell. This air freshener product, thus, has a relatively short longevity period. In addition, the character of such a perfume can can change over time as well. In most situations, it is desirable for the character of the perfume to remain substantially the same over time. This type of perfume release profile is typically provided when using hydrocarbon propellants, such as dimethyl ether (DME).

Figure 3:
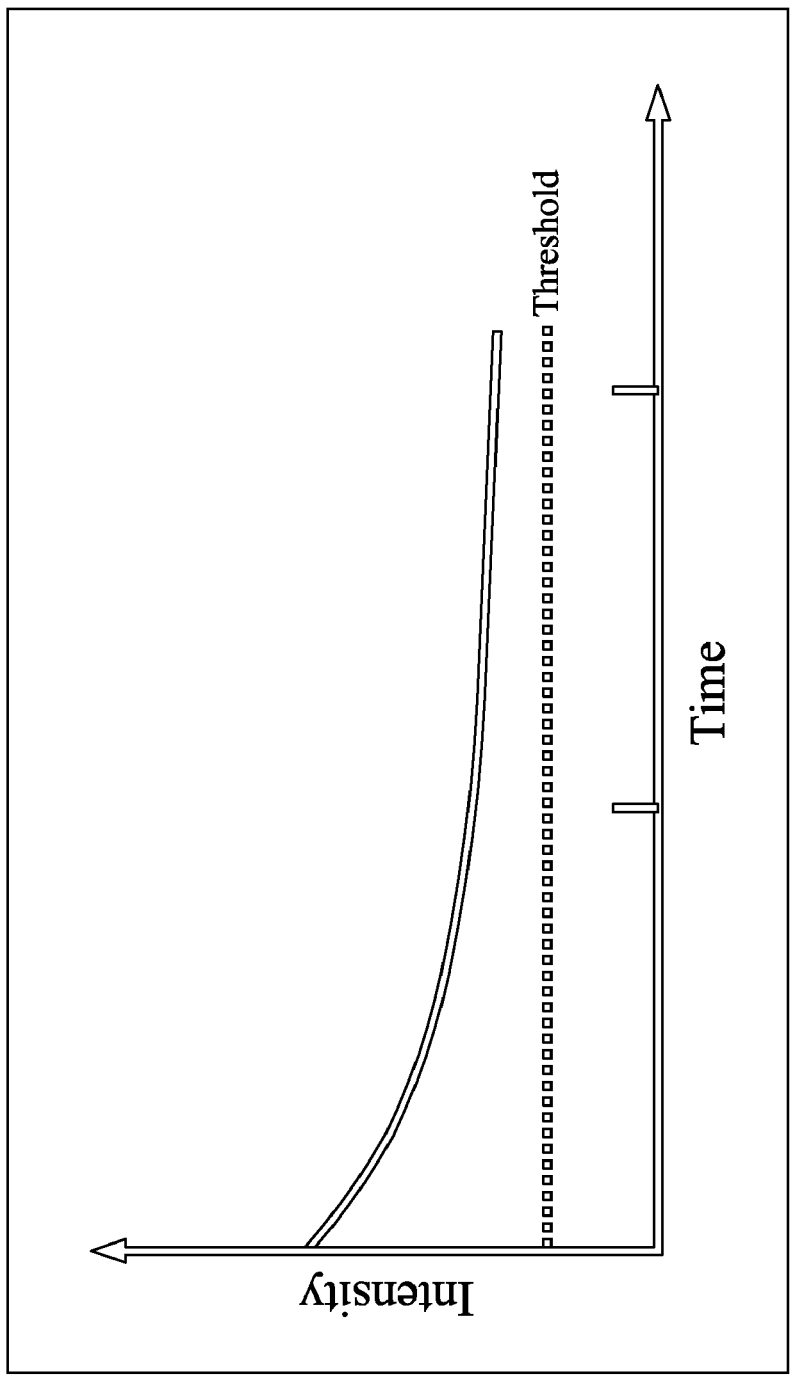
FIG. 3 is a graph of one non-limiting example of an air freshener having a more consistent perfume release profile, and longer period of longevity in the air.

FIG. 3 is a graph of one non-limiting example of an air freshener having a more consistent perfume release profile, and longer period of longevity in the air in which the perfume intensity remains over the detection threshold for a longer period of time. This type of perfume release profile can be provided by using a compressed gas, such as nitrogen, as a propellant. In certain embodiments, it is desirable for the air freshening composition to comprise a perfume having an initial intensity measured on a sensory rating scale of 0-5 (described in the Test Methods section below) that is less than or equal to (or merely less than) about 4, or about 3.5 within about two minutes after the composition is first dispersed. In these, or other embodiments, it may also be desirable for the perfume intensity of the air freshening composition to remain at a level greater than or equal to (or merely greater than) about 1, about 1.5, about 2, about 2.5, or about 3 after one or more of the following periods after the composition is first disbursed: 5, 10, 15, 20, 25, or minutes. In these or other embodiments, it may be desirable for the change in the intensity of the perfume composition over any of these periods of time to be less than or equal to (or merely less than): about 3.5, about 3, about 2.5, about 2, about 1.5, about 1, about 0.5, or about 0.

There are a number of ways to provide an air freshener with a consistent perfume release profile. In some cases, this can be a product of the perfume composition, and/or the manner in which the air freshening composition is distributed or dispersed into the air.

The perfume composition can be formulated so that it has characteristics that provide it with a more consistent release profile. Perfumes typically comprise one or more perfume ingredients. Often, these ingredients have different volatilities, boiling points, and odor detection thresholds. When a perfume composition is discharged into the air, the ingredients with the higher volatilities (referred to as "top notes") will be the ingredients that will volatilize and be detected by a person's sense of smell more quickly than the ingredients with lower volatilities (referred to as "middle notes") and the ingredients with the lowest volatility (referred to as "bottom notes"). This will cause the character of the perfume to change over time since after the perfume is first emitted, the overall perfume character will contain fewer and fewer top notes and more bottom notes.

In general, a perfume ingredient's character and volatility may be described in terms of its boiling point (or "B.P.") and its octanol/water partition coefficient (or "P"). The boiling point referred to herein is measured under normal standard pressure of 760 mmHg The boiling points of many perfume ingredients, at standard 760 mm Hg are given in, e.g., "Perfume and Flavor Chemicals (Aroma Chemicals)," written and published by Steffen Arctander, 1969.

The octanol/water partition coefficient of a perfume ingredient is the ratio between its equilibrium concentrations in octanol and in water. The partition coefficients of the perfume ingredients used in the air freshening composition may be more conveniently given in the form of their logarithm to the base 10, logP. The logP values of many perfume ingredients have been reported; see for example, the Pomona92 database, available from Daylight Chemical Information Systems, Inc. (Daylight CIS), Irvine, Calif. However, the logP values are most conveniently calculated by the "CLOGP" program, also available from Daylight CIS. This program also lists experimental logP values when they are available in the Pomona92 database. The "calculated logP" (ClogP) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990). The fragment approach is based on the chemical structure of each perfume ingredient, and takes into account the numbers and types of atoms, the atom connectivity, and chemical bonding. The ClogP values, which are the most reliable and widely used estimates for this physicochemical property, are preferably used instead of the experimental logP values in the selection of perfume ingredients for the air freshening composition.

The perfume composition may comprise perfume ingredients selected from one or more groups of ingredients. A first group of ingredients comprises perfume ingredients that have a boiling point of about 250° C. or less and ClogP of about 3 or less. More preferably, the first perfume ingredients have a boiling point of 240° C. or less, most preferably 235° C. or less. More preferably the first perfume ingredients have a ClogP value of less than 3.0, more preferably 2.5 or less. One or more ingredients from the first group of perfume ingredients can be present in any suitable amount in the perfume composition. In certain embodiments, the first perfume ingredient is present at a level of at least 1.0% by weight of the perfume composition, more preferably at least 3.5% and most preferably at least 7.0% by weight of the perfume composition.

A second group of perfume ingredients comprise perfume ingredients that have a boiling point of 250° C. or less and ClogP of 3.0 or more. More preferably the second perfume ingredients have a boiling point of 240° C. or less, most preferably 235° C. or less. More preferably, the second perfume ingredients have a ClogP value of greater than 3.0, even more preferably greater than 3.2. One or more ingredients from the second group of perfume ingredients can be present in any suitable amount in the perfume composition. In certain embodiments, the second perfume ingredient is present at a level of at least 10% by weight of the perfume composition, more preferably at least 15% and most preferably greater than 20% by weight of the perfume composition.

A third group of perfume ingredients comprises perfume ingredients that have a boiling point of 250° C. or more and ClogP of 3.0 or less. More preferably the third perfume ingredients have boiling point of 255° C. or more, most preferably 260° C. or more. More preferably, this additional perfume ingredient has a ClogP value of less than 3.0, more preferably 2.5 or less. One or more ingredients from the third group of perfume ingredients can be present in any suitable amount in the perfume composition. In certain embodiments, the third perfume ingredient is present at a level of at least 5.0% by weight of the perfume composition.

A fourth group of perfume ingredients comprises perfume ingredients that have a boiling point of 250° C. or more and ClogP of 3.0 or more. More preferably, this additional perfume ingredient has boiling point of 255° C. or more, most preferably 260° C. or more. More preferably, the additional perfume ingredient has a ClogP value of greater than 3.0, even more preferably greater than 3.2. One or more ingredients from the fourth group of perfume ingredients can be present in any suitable amount in the perfume composition. In certain embodiments, the fourth perfume ingredient is present at a level of at least 1% by weight of the perfume composition.

In one embodiment of the air freshening composition, the perfume composition comprises at least about 1% by weight of one or more volatile ingredients (from the first group of perfume ingredients) having a boiling point of less than or equal to about 250° C. and a Clog P value less than or equal to about 2.5. In another embodiment of the air freshening composition, the perfume composition comprises at least about 10% of one or more ingredients (from the second group of perfume ingredients) having a boiling point less than or equal to about 250° C. and Clog P value greater than or equal to about 3. In another embodiment of the air freshening composition, the perfume composition comprises at least about 5% of one or more ingredients (from the third group of perfume ingredients) having a boiling point of greater than or equal to about 250° C. and a Clog P value less than or equal to about 3. In another embodiment, the perfume composition comprises at least about 1% of one or more ingredients (from the fourth group of perfume ingredients) having a boiling point of greater than or equal to about 250° C. and a Clog P value greater than or equal to about 3. The perfume composition may also comprise any suitable combination of the embodiments described above.

For example, in another embodiment, the perfume composition comprises at least one perfume from the first group of perfume ingredients and at least one perfume from the second group of perfume ingredients. More preferably, the perfume composition comprises a plurality of ingredients chosen from the first group of perfume ingredients and a plurality of ingredients chosen from the second group of perfume ingredients. In order to extend the fragrance perception in the air, it is recommended to include a plurality of ingredients from the additional groups three and four to help round off the sensorial experience.

The perfume compositions useful in the air freshening composition can utilize relatively high levels of particularly chosen perfume ingredients. Such high levels of perfume had not previously been used because of a phenomenon known as the odor detection threshold. Perfume raw material generates an olfactory response in the individual smelling the perfume. The minimum concentration of perfume ingredient which is consistently perceived to generate an olfactory response in an individual, is known as the Odor Detection Threshold (ODT). As the concentration of perfume is increased, so is the odor intensity of the perfume, and the olfactory response of the individual. This is so until the concentration of the perfume reaches a maximum, at which point the odor intensity reaches a plateau beyond which there is no additional olfactory response by the individual. This range of perfume concentration through which the individual consistently perceives an odor is known as the Odor Detection Range (ODR).

It had been understood, until now, that the concentration of perfume ingredients in the perfume composition should be formulated within the ODR of the perfume ingredient, since compositions comprising higher levels provide no additional olfactory response and are thus costly and inefficient.

The Applicants have however found that in some circumstances it may be desirable to exceed the ODR of at least some of the perfume ingredient(s). The perfume is not only effusive and very noticeable when the product is used in an aqueous aerosol or pump spray, but it has also been found that the perfume continues diffusing from the multiple droplets disseminated on all surfaces within the room. The reservoir of perfume serves to replace diffused perfume, thus maintaining perfume concentration in the room at or beyond the odor detection threshold of the perfume throughout use, and preferably, after it has been initially sprayed or otherwise dispersed. Moreover, it has also been found that the perfume tends to linger for longer in the room in which the composition is used. Thus, in a preferred embodiment, at least one perfume ingredient selected from the first and/or second perfume ingredients is preferably present at a level of 50% in excess of the ODR, more preferably 150% in excess of the ODR. For very lingering perfume, at least one perfume ingredient can be added at a level of more than 300% of the ODR.

In certain embodiments, the perfume composition described herein can maintain a more consistent character over time. Larger droplet sizes (which have a smaller total surface area compared to a plurality of small droplets) can be used to reduce the speed with which the highly volatile top notes will volatilize. The droplets can not only release the perfume composition when they are suspended in the air, they can also fall until they contact a surface (e.g., tables or countertops, furniture, and floors, carpets, etc.). The droplets that fall onto these surfaces can serve as "reservoirs" for the perfume composition, and also release the perfume composition after landing on such surfaces. In this manner, there can be a continual renewal of the scent originally percieved by the consumer, which is replenished by molecules released from the droplets over a period of time. The mixing action of the heavier, higher Odor Detection Threshhold ("ODT") molecules (e.g., bottom notes such as musks, woody notes, etc.) with the newly released fresher more volatile lower ODT materials, will provide the consumer with a scent that is reminiscent of the one they initially experienced when the product was first applied.

Odor detection thresholds are determined using a commercial gas chromatograph ("GC") equipped with flame ionization and a sniff-port. The gas chromatograph is calibrated to determine the exact volume of material injected by the syringe, the precise split ratio, and the hydrocarbon response using a hydrocarbon standard of known concentration and chain-length distribution. The air flow rate is accurately measured and, assuming the duration of a human inhalation to last 12 seconds, the sampled volume is calculated. Since the precise concentration at the detector at any point in time is known, the mass per volume inhaled is known and concentration of the material can be caclulated. To determine whether a material has a threshold below 50 parts per billion (ppb), solutions are delivered to the sniff port at the back-calculated concentration. A panelist sniffs the GC effluent and identifies the retention time when odor is noticed. The average across all panelists determines the threshold of noticeability.

The necessary amount of analyte is injected onto the column to achieve a 50 ppb concentration at the detector. Typical gas chromatograph parameters for determining odor detection thresholds are listed below. The test is conducted according to the guidelines associated with the equipment.

Equipment:
GC: 5890 Series with FID detector (Agilent Technologies, Ind., Palo Alto, Calif., USA)
7673 Autosampler (Agilent Technologies, Ind., Palo Alto, Calif., USA)
Column: DB-1 (Agilent Technologies, Ind., Palo Alto, Calif., USA)
Length 30 meters ID 0.25 mm film thickness 1 micron (a polymer layer on the inner wall of the capillary tubing, which provide selective partitioning for separations to occur)

Method Parameters:
Split Injection: 17/1 split ratio
Autosampler: 1.13 microliters per injection
Column Flow: 1.10 mL/minute
Air Flow: 345 mL/minute
Inlet Temp. 245° C.
Detector Temp. 285° C.
Temperature Information
Initial Temperature: 50° C.
Rate: 5C/minute
Final Temperature: 280° C.
Final Time: 6 minutes
Leading assumptions: (i) 12 seconds per sniff
(ii) GC air adds to sample dilution The first and second perfume ingredients may comprise, among other things: esters, ketones, aldehydes, alcohols, derivatives thereof and mixtures thereof. Table 1 provides some non-limiting examples of first perfume ingredients and Table 2 provides some non-limiting examples of second perfume ingredients.

TABLE 1

Examples of First Perfume Ingredients

| Perfume Ingredients | Approx. BP (° C.) | Approx. ClogP |
|---|---|---|
| Allyl Caproate | 185 | 2.772 |
| Amyl Acetate | 142 | 2.258 |
| Amyl Propionate | 161 | 2.657 |
| Anisic Aldehyde | 248 | 1.779 |
| Anisole | 154 | 2.061 |
| Benzaldehyde | 179 | 1.480 |
| Benzyl Acetate | 215 | 1.960 |
| Benzyl Acetone | 235 | 1.739 |
| Benzyl Alcohol | 205 | 1.100 |
| Benzyl Formate | 202 | 1.414 |
| Benzyl Iso Valerate | 246 | 2.887 |
| Benzyl Propionate | 222 | 2.489 |

TABLE 1-continued

Examples of First Perfume Ingredients

| Perfume Ingredients | Approx. BP (° C.) | Approx. ClogP |
|---|---|---|
| Beta Gamma Hexenol | 157 | 1.337 |
| Camphor Gum | 208 | 2.117 |
| laevo-Carveol | 227 | 2.265 |
| d-Carvone | 231 | 2.010 |
| laevo-Carvone | 230 | 2.203 |
| Cinnamyl Formate | 250 | 1.908 |
| Cis-Jasmone | 248 | 2.712 |
| Cis-3-Hexenyl Acetate | 169 | 2.243 |
| Cuminic alcohol | 248 | 2.531 |
| Cuminic aldehyde | 236 | 2.780 |
| Cyclal C | 180 | 2.301 |
| Dimethyl Benzyl Carbinol | 215 | 1.891 |
| Dimethyl Benzyl Carbinyl Acetate | 250 | 2.797 |
| Ethyl Acetate | 77 | 0.730 |
| Ethyl Aceto Acetate | 181 | 0.333 |
| Ethyl Amyl Ketone | 167 | 2.307 |
| Ethyl Benzoate | 212 | 2.640 |
| Ethyl Butyrate | 121 | 1.729 |
| Ethyl Hexyl Ketone | 190 | 2.916 |
| Ethyl-2-methyl butyrate | 131 | 2.100 |
| Ethyl-2-Methyl Pentanoate | 143 | 2.700 |
| Ethyl Phenyl Acetate | 229 | 2.489 |
| Eucalyptol | 176 | 2.756 |
| Fenchyl Alcohol | 200 | 2.579 |
| Flor Acetate (tricyclo Decenyl Acetate) | 175 | 2.357 |
| Frutene (tricyclo Decenyl Propionate) | 200 | 2.260 |
| Geraniol | 230 | 2.649 |
| Hexenol | 159 | 1.397 |
| Hexenyl Acetate | 168 | 2.343 |
| Hexyl Acetate | 172 | 2.787 |
| Hexyl Formate | 155 | 2.381 |
| Hydratropic Alcohol | 219 | 1.582 |
| Hydroxycitronellal | 241 | 1.541 |
| Isoamyl Alcohol | 132 | 1.222 |
| Isomenthone | 210 | 2.831 |
| Isopulegyl Acetate | 239 | 2.100 |
| Isoquinoline | 243 | 2.080 |
| Ligustral | 177 | 2.301 |
| Linalool | 198 | 2.429 |
| Linalool Oxide | 188 | 1.575 |
| Linalyl Formate | 202 | 2.929 |
| Menthone | 207 | 2.650 |
| Methyl Acetophenone | 228 | 2.080 |
| Methyl Amyl Ketone | 152 | 1.848 |
| Methyl Anthranilate | 237 | 2.024 |
| Methyl Benzoate | 200 | 2.111 |
| Methyl Benzyl Acetate | 213 | 2.300 |
| Methyl Eugenol | 249 | 2.783 |
| Methyl Heptenone | 174 | 1.703 |
| Methyl Heptine Carbonate | 217 | 2.528 |
| Methyl Heptyl Ketone | 194 | 1.823 |
| Methyl Hexyl Ketone | 173 | 2.377 |
| Methyl Phenyl Carbinyl Acetate | 214 | 2.269 |
| Methyl Salicylate | 223 | 1.960 |
| Nerol | 227 | 2.649 |
| Octalactone | 230 | 2.203 |
| Octyl Alcohol (Octanol-2) | 179 | 2.719 |
| para-Cresol | 202 | 1.000 |
| para-Cresyl Methyl Ether | 176 | 2.560 |
| para-Methyl Acetophenone | 228 | 2.080 |
| Phenoxy Ethanol | 245 | 1.188 |
| Phenyl Acetaldehyde | 195 | 1.780 |
| Phenyl Ethyl Acetate | 232 | 2.129 |
| Phenyl Ethyl Alcohol | 220 | 1.183 |
| Phenyl Ethyl Dimethyl Carbinol | 238 | 2.420 |
| Prenyl Acetate | 155 | 1.684 |
| Propyl Butyrate | 143 | 2.210 |
| Pulegone | 224 | 2.350 |
| Rose Oxide | 182 | 2.896 |
| Safrole | 234 | 1.870 |
| 4-Terpinenol | 212 | 2.749 |
| alpha-Terpineol | 219 | 2.569 |
| Viridine | 221 | 1.293 |

TABLE 2

Examples of Second Perfume Ingredients

| Perfume Ingredients | Approx. BP (° C.) | Approx. ClogP |
|---|---|---|
| allo-Ocimene | 192 | 4.362 |
| Allyl Heptoate | 210 | 3.301 |
| Anethol | 236 | 3.314 |
| Benzyl Butyrate | 240 | 3.698 |
| Camphene | 159 | 4.192 |
| Carvacrol | 238 | 3.401 |
| cis-3-Hexenyl Tiglate | 101 | 3.700 |
| Citral (Neral) | 228 | 3.120 |
| Citronellol | 225 | 3.193 |
| Citronellyl Acetate | 229 | 3.670 |
| Citronellyl Isobutyrate | 249 | 4.937 |
| Citronellyl Nitrile | 225 | 3.094 |
| Citronellyl Propionate | 242 | 4.628 |
| Cyclohexyl Ethyl Acetate | 187 | 3.321 |
| Decyl Aldehyde | 209 | 4.008 |
| Delta Damascone | 242 | 3.600 |
| Dihydro Myrcenol | 208 | 3.030 |
| Dihydromyrcenyl Acetate | 225 | 3.879 |
| Dimethyl Octanol | 213 | 3.737 |
| Fenchyl Acetate | 220 | 3.485 |
| gamma Methyl Ionone | 230 | 4.089 |
| gamma-Nonalactone | 243 | 3.140 |
| Geranyl Acetate | 245 | 3.715 |
| Geranyl Acetone | 216 | 3.269 |
| Geranyl Isobutyrate | 245 | 4.393 |
| Geranyl Nitrile | 222 | 3.139 |
| Hexenyl Isobutyrate | 182 | 3.181 |
| Hexyl Neopentanoate | 224 | 4.374 |
| Hexyl Tiglate | 231 | 3.800 |
| alpha-Ionone | 237 | 3.381 |
| beta-Ionone | 239 | 3.960 |
| gamma-Ionone | 240 | 3.780 |
| alpha-bone | 250 | 3.820 |
| Isobornyl Acetate | 227 | 3.485 |
| Isobutyl Benzoate | 242 | 3.028 |
| Isononyl Acetate | 200 | 3.984 |
| Isononyl Alcohol | 194 | 3.078 |
| Isomenthol | 219 | 3.030 |
| para-Isopropyl Phenylacetaldehyde | 243 | 3.211 |
| Isopulegol | 212 | 3.330 |
| Lauric Aldehyde (Dodecanal) | 249 | 5.066 |
| d-Limonene | 177 | 4.232 |
| Linalyl Acetate | 220 | 3.500 |
| Menthyl Acetate | 227 | 3.210 |
| Methyl Chavicol | 216 | 3.074 |
| alpha-iso "gamma" Methyl Ionone | 230 | 4.209 |
| Methyl Nonyl Acetaldehyde | 232 | 4.846 |
| Methyl Octyl Acetaldehyde | 228 | 4.317 |
| Myrcene | 167 | 4.272 |
| Neral | 228 | 3.120 |
| Neryl Acetate | 231 | 3.555 |
| Nonyl Acetate | 212 | 4.374 |
| Nonyl Aldehyde | 212 | 3.479 |
| Octyl Aldehyde | 223 | 3.845 |
| Orange Terpenes (d-Limonene) | 177 | 4.232 |
| para-Cymene | 179 | 4.068 |
| Phenyl Ethyl Isobutyrate | 250 | 3.000 |
| alpha-Pinene | 157 | 4.122 |
| beta-Pinene | 166 | 4.182 |
| alpha-Terpinene | 176 | 4.412 |
| gamma-Terpinene | 183 | 4.232 |
| Terpinolene | 184 | 4.232 |
| Terpinyl acetate | 220 | 3.475 |
| Tetrahydro Linalool | 191 | 3.517 |
| Tetrahydro Myrcenol | 208 | 3.517 |
| Undecenal | 223 | 4.053 |
| Veratrol | 206 | 3.140 |
| Verdox | 221 | 4.059 |
| Vertenex | 232 | 4.060 |

Table 3 provides some non-limiting examples of the third and fourth group of perfume ingredients which have a B.P. of greater than or equal to about 250° C.

TABLE 3

Examples of Optional Perfume Ingredients

| Perfume Ingredients | Approximate B.P. (° C.) | Approximate ClogP |
|---|---|---|
| Allyl Cyclohexane Propionate | 267 | 3.935 |
| Ambrettolide | 300 | 6.261 |
| Amyl Benzoate | 262 | 3.417 |
| Amyl Cinnamate | 310 | 3.771 |
| Amyl Cinnamic Aldehyde | 285 | 4.324 |
| Amyl Cinnamic Aldehyde Dimethyl Acetal | 300 | 4.033 |
| iso-Amyl Salicylate | 277 | 4.601 |
| Aurantiol | 450 | 4.216 |
| Benzophenone | 306 | 3.120 |
| Benzyl Salicylate | 300 | 4.383 |
| Cadinene | 275 | 7.346 |
| Cedrol | 291 | 4.530 |
| Cedryl Acetate | 303 | 5.436 |
| Cinnamyl Cinnamate | 370 | 5.480 |
| Coumarin | 291 | 1.412 |
| Cyclohexyl Salicylate | 304 | 5.265 |
| Cyclamen Aldehyde | 270 | 3.680 |
| Dihydro Isojasmonate | 300 | 3.009 |
| Diphenyl Methane | 262 | 4.059 |
| Ethylene Brassylate | 332 | 4.554 |
| Ethyl Methyl Phenyl Glycidate | 260 | 3.165 |
| Ethyl Undecylenate | 264 | 4.888 |
| iso-Eugenol | 266 | 2.547 |
| Exaltolide | 280 | 5.346 |
| Galaxolide | 260 | 5.482 |
| Geranyl Anthranilate | 312 | 4.216 |
| Hexadecanolide | 294 | 6.805 |
| Hexenyl Salicylate | 271 | 4.716 |
| Hexyl Cinnamic Aldehyde | 305 | 5.473 |
| Hexyl Salicylate | 290 | 5.260 |
| Linalyl Benzoate | 263 | 5.233 |
| 2-Methoxy Naphthalene | 275 | 3.235 |
| Methyl Cinnamate | 263 | 2.620 |
| Methyl Dihydrojasmonate | 300 | 2.275 |
| beta-Methyl Naphthyl ketone | 300 | 2.275 |
| Musk Indanone | 250 | 5.458 |
| Musk Ketone | M.P.[1] = 137 | 3.014 |
| Musk Tibetine | M.P. = 136 | 3.831 |
| Myristicin | 276 | 3.200 |
| delta-Nonalactone | 280 | 2.760 |
| Oxahexadecanolide-10 | 300 | 4.336 |
| Oxahexadecanolide-11 | M.P. = 35 | 4.336 |
| Patchouli Alcohol | 285 | 4.530 |
| Phantolide | 288 | 5.977 |
| Phenyl Ethyl Benzoate | 300 | 4.058 |
| Phenylethylphenylacetate | 325 | 3.767 |
| alpha-Santalol | 301 | 3.800 |
| Thibetolide | 280 | 6.246 |
| delta-Undecalactone | 290 | 3.830 |
| gamma-Undecalactone | 297 | 4.140 |
| Vanillin | 285 | 1.580 |
| Vetiveryl Acetate | 285 | 4.882 |
| Yara-Yara | 274 | 3.235 |

[1]"M.P." is melting point (in degrees C.); these ingredients have a B.P. higher than 275° C.

In the perfume art, some auxiliary materials having no odor, or a low odor, are used, e.g., as solvents, diluents, extenders or fixatives. Non-limiting examples of these materials are ethyl alcohol, carbitol, diethylene glycol, dipropylene glycol, diethyl phthalate, triethyl citrate, isopropyl myristate, and benzyl benzoate. These materials are used for, e.g., solubilizing or diluting some solid or viscous perfume ingredients to, e.g., improve handling and/or formulating. These materials are useful in the perfume compositions, but are not counted in the calculation of the limits for the definition/formulation of the perfume compositions used herein.

It can be desirable to use perfume ingredients and even other ingredients, preferably in small amounts, in the perfume compositions described herein, that have low odor detection threshold values. The odor detection threshold of an odorous material is the lowest vapor concentration of that material which can be detected. The odor detection threshold and some odor detection threshold values are discussed in, e.g., "Standardized Human Olfactory Thresholds", M. Devos et al, IRL Press at Oxford University Press, 1990, and "Compilation of Odor and Taste Threshold Values Data", F. A. Fazzalari, editor, ASTM Data Series DS 48A, American Society for Testing and Materials, 1978. The use of small amounts of perfume ingredients that have low odor detection threshold values can improve perfume character such as by adding complexity to the perfume character to "round off" the fragrance. Examples of perfume ingredients that have low odor detection threshold values useful in the perfume composition include, but are not limited to: coumarin, vanillin, ethyl vanillin, methyl dihydro isojasmonate, 3-hexenyl salicylate, isoeugenol, lyral, gamma-undecalactone, gamma-dodecalactone, methyl beta naphthyl ketone, and mixtures thereof. These materials can be present at any suitable level. In some embodiments, these materials may be present at low levels in the perfume composition, typically less than 5%, preferably less than 3%, more preferably less than 2%, by weight of the perfume composition.

EXAMPLES

The following examples numbered A to H, are non-limiting examples of suitable perfume compositions.

| Perfume ingredient | A | B | C | D | E | F | G | H |
|---|---|---|---|---|---|---|---|---|
| Allyl Caproate | 2 | — | — | 4 | — | 2 | — | 3 |
| Citronellyl Acetate | 5 | 8 | 6 | 3 | 5 | 6 | 5 | 3 |
| Delta Damascone | 1 | 0.5 | 0.9 | 3 | 0.8 | 2 | 0.6 | 1 |
| Ethyl-2-methyl Butyrate | 8 | 2 | 1.5 | 12 | 1.5 | 15 | 1 | 11 |
| Flor Acetate | 8 | — | — | 4 | — | 4 | — | 5 |
| Frutene | 4 | — | — | 8 | — | 4 | — | 8 |
| Geranyl Nitrile | 1 | 15 | 22 | 1 | 28 | 1 | 32 | 5 |
| Ligustral | 6 | 7.5 | 12 | 10 | 8 | 13 | 8 | 10 |
| Methyl dihydro Jasmonate | 27.69 | 37.36 | 21.89 | 25 | 28.04 | 30 | 25.70 | 25.59 |
| Nectaryl | 5 | — | — | 3 | — | 4 | — | 3 |
| Neobutanone | 0.30 | 0.09 | 0.12 | 0.3 | 0.1 | 0.2 | 0.15 | 0.4 |
| Oxane | 0.01 | 0.05 | 0.09 | 0.01 | 0.06 | 0.01 | 0.05 | 0.01 |
| Tetrahydro Linalool | 32 | — | — | 26.69 | — | 18.79 | — | 25 |
| Methyl nonyl acetaldehyde | — | 7 | 15 | — | 10 | — | 8.5 | — |
| Ethyl-2-methyl pentanoate | — | 1 | 1.5 | — | 1 | — | 1 | — |
| Iso E Super | — | 3 | 2 | — | 3 | — | 3 | — |
| Ionone beta | — | 1.5 | 2 | — | 1.5 | — | 1 | — |
| Habanolide | — | 3 | 3 | — | 3 | — | 3 | — |
| Geraniol | — | 15 | 12 | — | 10 | — | 11 | — |

In other embodiments, the air freshening composition can be dispersed in a manner that provides it with a more consistent release profile. The air freshening composition can be sprayed into the air. Any suitable type of article can be used to spray the air freshening composition into the air. The air freshening composition can be sprayed using any suitable type of sprayer. One suitable type of sprayer is an aerosol sprayer. If an aerosol sprayer is used, it can use any suitable type of propellant. The propellant can include hydrocarbon propellants, or non-hydrocarbon propellants. In some embodiments, it is desirable to use propellants that are primarily non-hydrocarbon propellants (that is, propellants that are comprised of more non-hydrocarbon propellants by volume than hydrocarbon propellants. In some embodiments, the propellant may be substantially free of hydrocarbons such as: isobutene, butane, isopropane, and dimethyl ether (DME).

Figure 4:
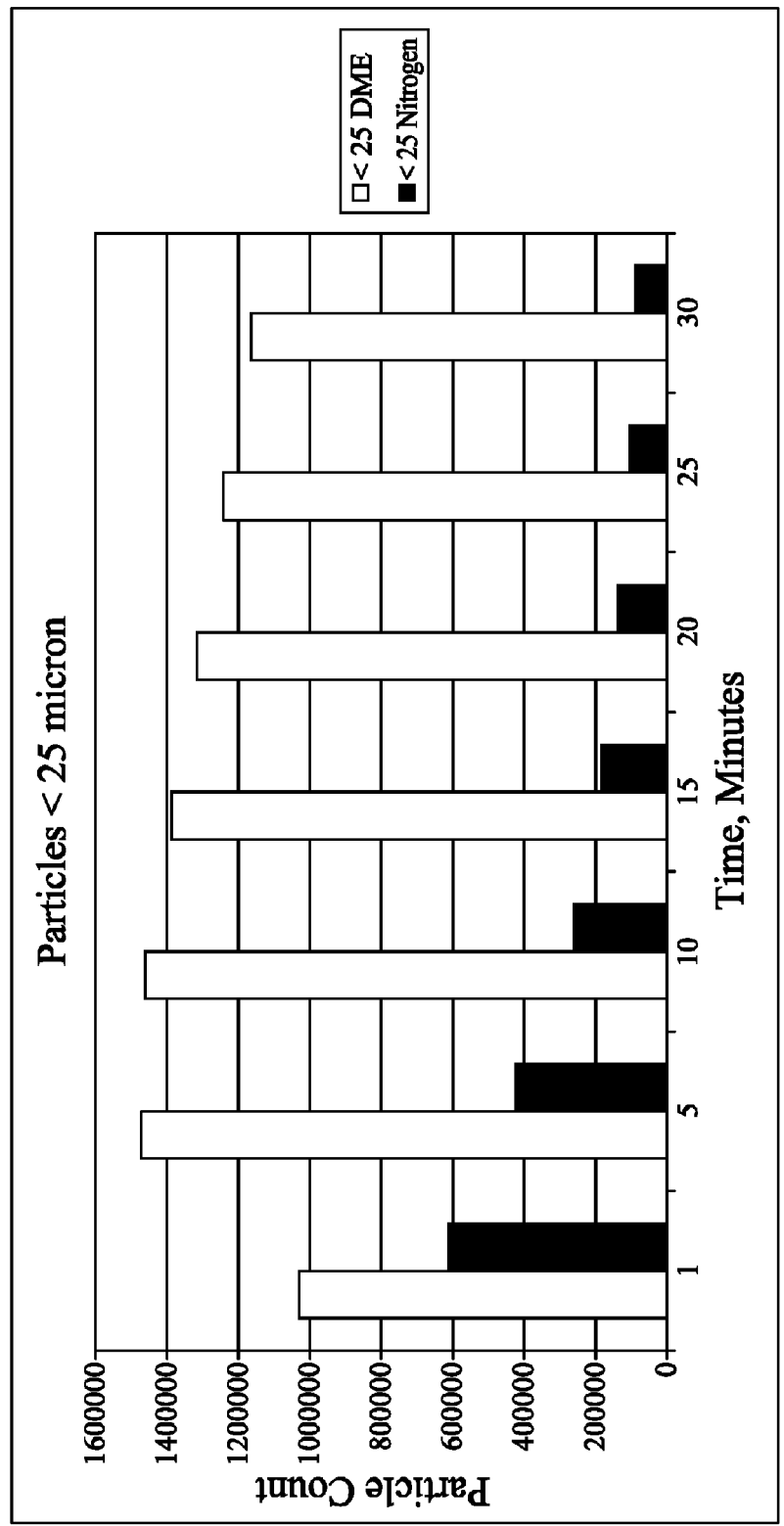
FIG. 4 is a bar graph showing the relatively higher amount of small droplets in a spray that uses dimethyl ether (DME) hydrocarbon as a propellant in comparison to a spray that uses nitrogen as a propellant.

Without wishing to bound by any particular theory, it is believed that one of the reasons that some air fresheners that are dispersed from aerosol cans that utilize hydrocarbon propellants have undesirable release profiles that are characterized by an overwhelming initial burst of scent, and the scent has short longevity in the air, is that sprays from cans that use hydrocarbon as a propellant contain a large number of small droplets of the composition. The large number of small droplets of composition provide a large amount of surface area for exposing the air freshening composition to the air, which is believed to allow the scent to rapidly volatilize, and contribute to the overwhelming initial burst of scent and short longevity of the same. FIG. 4 shows a comparison of the relatively higher amount of small droplets in a spray that uses dimethyl ether (DME) hydrocarbon as a propellant in comparison to a spray that uses nitrogen as a propellant.

Therefore, in some embodiments, it may be desirable for the air freshener to be dispersed from a container that uses a non-hydrocarbon propellant. Such a propellant may include, but is not limited to compressed gas. In addition, some compressed gases can be more environmentally-friendly than hydrocarbon propellants, which may make them more suitable for actual air freshening. Suitable compressed gases include, but are not limited to compressed air, nitrogen, nitrous oxide, inert gases, carbon dioxide, etc., and mixtures thereof.

In one version of such an embodiment, at least some of the spray droplets are sufficiently small in size to be suspended in the air for at least about 10 minutes, and in some cases, for at least about 15 minutes, or at least about 30 minutes. The spray droplets can be of any suitable size. In some embodiments, at least some of the spray droplets have a diameter in a range of from about 0.01 µm to about 500 µm, or from about 5 µm to about 400 µm, or from about 10 µm to about 200 µm. The mean particle size of the spray droplets may be in the range of from about 10 µm to about 100 µm, or from about 20 µm-about 60 µm.

Although compressed gas systems produce large particles that generate a more desirable perfume release profile, these same particles can create wetness on the floor and other surfaces because they are heavier and fall to the ground. In one embodiment of the present invention, the total product output and the spray droplet/particle size distribution are selected to support the perfume efficacy but avoid a surface wetness problem. Total product output is determined by the flow rate of the product as it is released from the container. To achieve a spray profile that produces minimal surface wetness, it is desirable to have a low flow rate and small spray droplets. In a preferred embodiment, the flow rate will be less than 1.2 grams/second and the droplets will be small enough that when, dispensed at a height of 5 feet from the ground, less than 40 percent of the droplets fall to the ground. More preferably, the droplets will be small enough that when, dispensed at a height of 5 feet from the ground, less than 35 percent of the droplets fall to the ground. Even more preferably, the droplets will be small enough that when, dispensed at a height of 5 feet from the ground, less than 30 percent of the droplets fall to the ground.

A low flow rate can be achieved via the valve, the delivery tube and/or the nozzle but nozzle modifications have proven to be less susceptible to instances of clogging. Small particles can be efficiently created when the spray is dispensed in a wide cone angle. For a given nozzle component and delivery tube, cone angles can be modified by varying the insertion depth of the nozzle in the delivery tube. In a preferred embodiment, the cone angle will be greater than about 20 degrees. More preferably, the cone angle will be greater than about 30 degrees, still more preferably, it will be greater than about 35 degrees. Even more preferably, the cone angle will be greater than about 40 degrees, and more preferably, it will be greater than about 50 degrees.

When a non-hydrocarbon propellant is used, the flow rate of the air freshening composition as it exits the dispensing device becomes important. The flow rate should be low enough to prevent the formation of large spray droplets. For purposes of this application, flow rate is determined by measuring the rate of product expelled by a full container of product for the first 60 seconds of use. In a preferred embodiment, the flow rate of the air freshening composition being released from the container is from about 0.0001 grams/second to about 1.2 grams/second. More preferably, the flow rate is from about 0.001 grams/second to about 1.1 grams/second. Even more preferably, the flow rate is from about 0.01 grams/second to about 1.0 grams/second. Still more preferably, the flow rate is from about 0.1 grams/second to about 1.1 grams/second. More preferably yet, the flow rate is from about 0.1 grams/second to about 1.0 grams/second. In an alternate embodiment, the flow rate is from about 0.1 grams/second to about 0.9 grams/second, alternatively from about 0.8 grams/second to about 1.5 grams/second.

The air freshening composition can be packaged in any suitable container. Preferably, the container holds at least about 120 grams of air freshening composition. More preferably, the container holds at least about 130 grams of air freshening composition, still more preferably, it holds at least about 150 grams of air freshening composition. Suitable containers include aerosol cans. In a preferred embodiment, the container is not a bag-in-can system. In one embodiment, the aerosol can may have a dispenser that sprays the air freshening composition at an angle that is between an angle that is parallel to the base of the container and an angle that is perpendicular thereto in order to facilitate spraying the product into the air. In addition to sprayers that use compressed gas as a propellant, in other embodiments, the desired size of spray droplets can be delivered by other types of devices that are capable of being set to provide a narrow range of droplet size. Such other devices include, but are not limited to: foggers, ultrasonic nebulizers, electrostatic sprayers, and spinning disk sprayers.

Malodor Control

The air freshening product may also deliver a genuine malodor removal benefit. A genuine malodor removal benefit is defined as both a sensory and analytically measurable (such as by gas chromatograph) malodor reduction. Thus, if the air freshening product delivers a genuine malodor removal benefit, the air freshening product will not function merely by using perfume to cover up or mask odors. However, it is also contemplated herein that some embodiments of the air freshening product may function either partially, or entirely by masking odors. If the air freshening product is provided with a malodor counteractant, the air freshening product may utilize one or more of several types of odor control mechanisms.

Malodor Neutralization

One type of air freshening composition utilizes a malodor neutralization via vapor phase technology. The vapor phase technology is defined as malodor counteractants that mitigate malodors in the air via chemical reactions or neutralization. More preferably, the malodor counteractants are safe for fabrics.

In one embodiment of a composition that utilizes vapor phase technology, the air freshening composition comprises one or more fabric-safe aliphatic aldehydes and/or one or more enones (ketones with unsaturated double bonds). It may also be desirable for these vapor phase technologies to have virtually no negative impact on the desired perfume character. Certain malodor technologies are odoriforess and negatively impact the overall character of the fragrance. In this case, a perfume/malodor counteractant premix is formed such that the perfume raw materials used in this technology are selected to neutralize any odor of the malodor counteractants. This odor neutralized premix can then be added to a parent perfume without affecting the character of the parent fragrance. This permits the vapor phase technology to be used broadly with a large variety of fragrance types. In addition, types of vapor phase technologies that predominately comprise a straight chain aliphatic backbone will not discolor fabrics, unlike products that utilize types of aldehydes that contain multiple double bonds and benzene rings.

The malodor counteractants that utilize vapor phase technology can be present in any suitable amount in the perfume composition. In certain embodiments, the malodor counteractants may be present in an amount greater than or equal to about 1% and less than about 50% by weight of the perfume composition. In other embodiments, the malodor counteractants may be present in an amount greater than or equal to about 3% and less than about 30% by weight of the perfume composition. In other embodiments, the malodor counteractants may be present in an amount greater than or equal to about 8% and less than about 15% by weight of the perfume composition.

The following table illustrates the importance of proper selction of aldehydes and enones to avoid fabric yellowing.

| Aldehyde Solution Tested | Fadometer Test on treated Fabric (0.75 grams of product are pipetted onto a 4 inch x 4 inch (10 cm x 10 cm) swatch which is then subjected to 5 hours of exposure to simulated sunlight using a SUNTEST CPS+ model Fadometer supplied by Atlas, Chicago, Illinois, USA. |
|---|---|
| Control - untreated fabric swatch | No yellowing |
| 1000 ppm amylic cinnamic aldehyde (aromatic) | Yellowish brown |
| 1000 ppm citronellal (aromatic) | Yellowish brown |
| 1000 ppm citral aldehyde (aliphatic) | No yellowing |
| 1000 ppm lauric aldehyde (aliphatic) | No yellowing |

Examples of suitable aliphatic aldehydes are R—COH where R is saturated $C_7$ to $C_{22}$ linear and/or branched with no more than two double bonds. Additional examples of aliphatic aldehydes are lyral, methyl dihydro jasmonate, ligustral, melonal, octyl aldehyde, citral, cymal, nonyl aldehyde, bourgeonal, P. T. Bucinal, Decyl aldehydes, lauric aldehyde, and mixtures thereof. Examples of suitable enones are ionone alpha, ionone beta, ionone gamma methyl, and mixtures thereof. The malodor counteractant can comprise one or more aliphatic aldehydes, one or more enones, or any combination thereof. The following are several non-limiting examples of perfume formulations that include fabric-safe vapor phase malodor counteractants.

Examples of Perfume Compositions with Malodor Counteractants

(1) Pine

| Material Name | Amount |
| --- | --- |
| Rosemary | 10.00 |
| Spike Lavender | 10.00 |
| Lavandin Grosso | 5.00 |
| Spruce (conf.-manh) | 5.00 |
| Camphor Gum | 5.00 |
| Melonal | 0.30 |
| Eucalyptol | 15.00 |
| Iso Menthone | 15.00 |
| Iso Bornyl Acetate | 21.70 |
| Ionone Beta | 8.00 |
| Iso E Super | 5.00 |
| | 100.00 |

(2) Ozonic

| Material Name | Amount |
| --- | --- |
| Xi Aldehyde | 8.00 |
| 2' 6 Nonadienol 10% In Dpg | 5.00 |
| Helional | 13.00 |
| Hydroxycitronellal | 11.50 |
| Calone 1951 | 0.50 |
| 2' 6-Nonadien-1-al/10% In Dpg | 5.00 |
| Lyral | 20.00 |
| Melonal | 1.00 |
| Iso Menthone | 10.00 |
| Floralozone | 10.00 |
| Bourgeonal | 10.00 |
| Delta Muscenone 962191 | 1.00 |
| Habanolide 100% | 5.00 |
| | 100.00 |

(3) Fruity

| Material Name | Amount |
| --- | --- |
| Fruitate | 5.00 |
| Orange Terpenes | 13.00 |
| Ethyl Acetoacetate | 3.00 |
| 2' 6 Nonadienol 10% In Dpg | 1.00 |
| Ethyl Acetate | 3.00 |
| Benzaldehyde | 2.00 |
| Prenyl Acetate | 8.00 |
| Benzyl Acetate | 15.00 |
| 2' 6-Nonadien-1-al/10% In Dpg | 1.00 |
| Ethyl-2-methyl Butyrate | 8.00 |
| Amyl Acetate | 3.00 |
| Cis 3 Hexenyl Acetate | 3.00 |
| Methyl Dihydro Jasmonate | 10.00 |
| Ligustral | 5.00 |
| Melonal | 1.00 |
| Ethyl 2 Methyl Pentanoate | 8.00 |
| Hexyl Acetate | 8.00 |
| Habanolide 100% | 3.00 |
| | 100.00 |

(4) Citrus

| Material Name | Amount |
| --- | --- |
| Orange Terpenes | 20.00 |
| Lemon Terpenes X5 Fold | 20.00 |
| Lime Oil Cf-8-1285-1 (conf.-berje) | 10.00 |
| Grapefruit Phase C - Ref. N*12245 | 20.00 |
| Italian Orange Phase Oil | 22.90 |
| Delta Muscenone 962191 | 0.50 |
| Oxane | 0.30 |
| Iso Menthone | 1.00 |
| Rhubafuran | 0.30 |
| Habanolide 100% | 5.00 |
| | 100.00 |

(5) Floral

| Material Name | Amount |
| --- | --- |
| Spike Lavender | 5.00 |
| Rosemary | 5.00 |
| Helional | 10.00 |
| Hydroxycitronellal | 10.00 |
| Benzyl Acetate | 9.30 |
| Lyral | 20.00 |
| Ligustral | 2.00 |
| Melonal | 0.20 |
| Eucalyptol | 2.00 |
| Iso Menthone | 8.00 |
| Bourgeonal | 20.00 |
| Undecavertol | 3.00 |
| Delta Muscenone 962191 | 0.50 |
| Habanolide 100% | 5.00 |
| | 100.00 |

In certain cases, fabrics that are laundered will have residual brighteners deposited from detergents with which they are washed. Therefore, it may be desirable for the reactive aldehydes to be compatible with brighteners so that the air freshening composition will not discolor any fabrics with which it comes into contact. A number of the examples above are compatible with brighteners.

Figure 5:
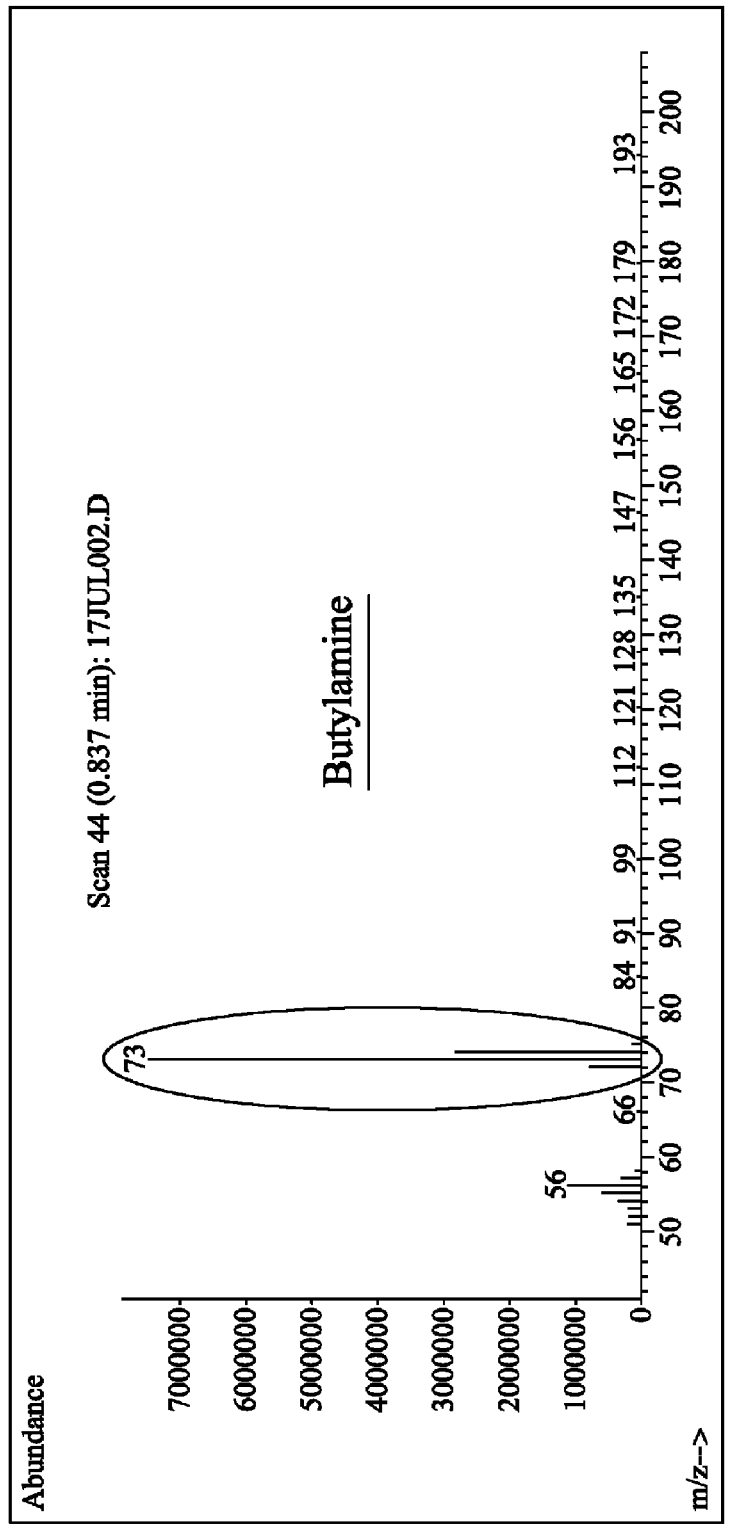
FIG. 5 is a print out from a gas chromatograph that shows the presence of butylamine (a fish odor) in the air.
Figure 6:
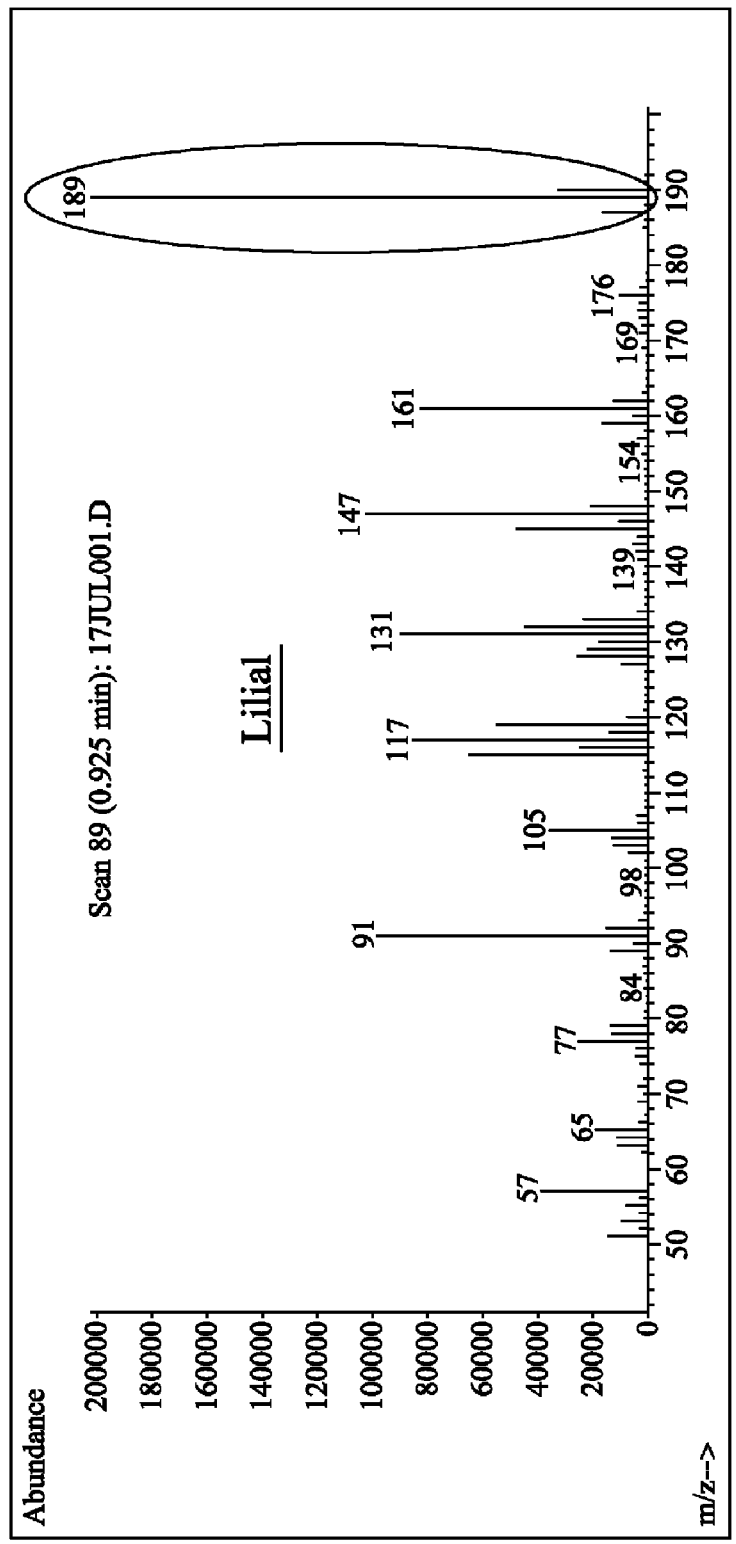
FIG. 6 is a print out from a gas chromatograph that shows the presence of Lilial (an aldehyde) in the air.
Figure 7:
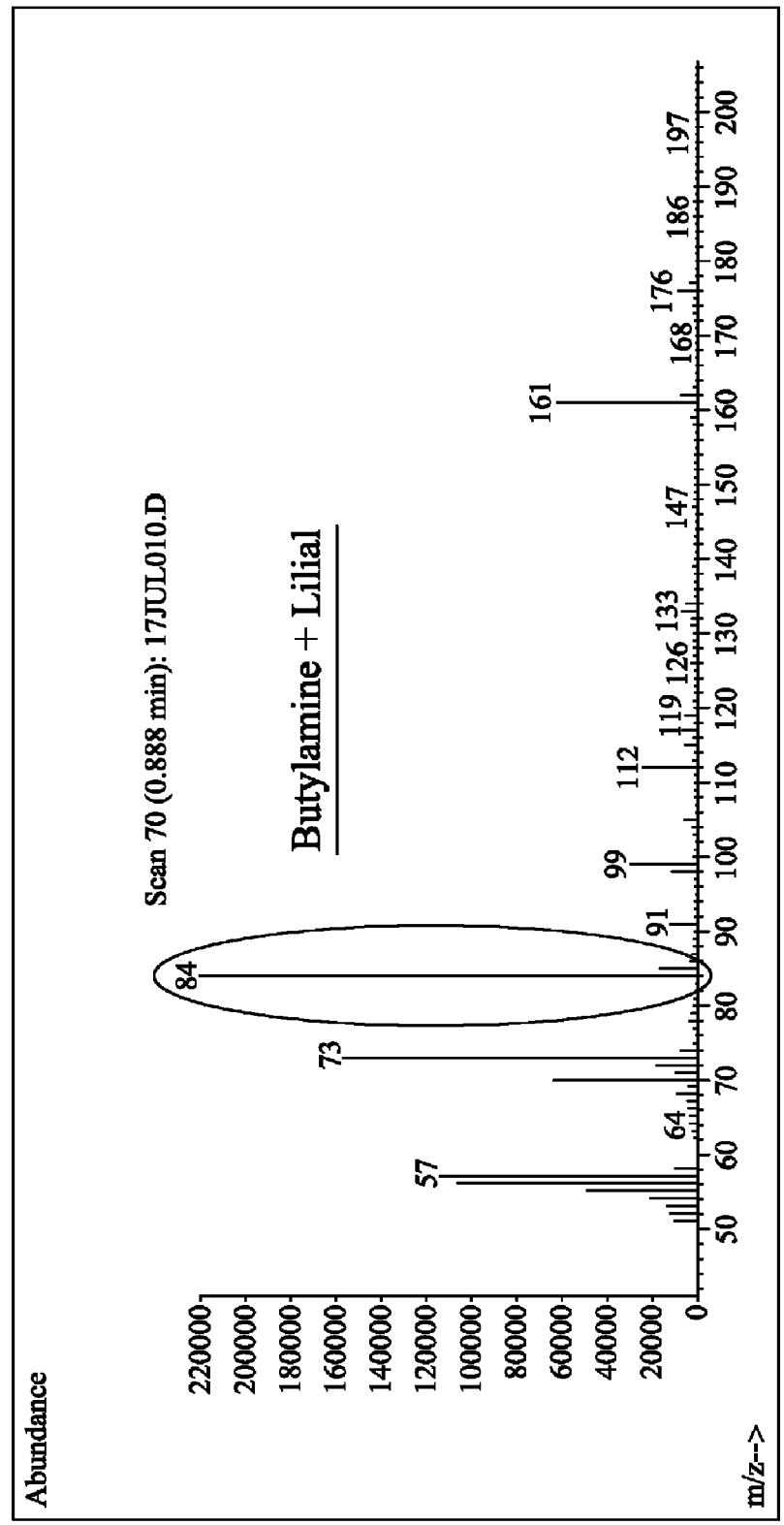
FIG. 7 is a print out from a gas chromatograph that shows what happens when the two substances are combined.

In a number of the examples above, the air freshening composition comprises a mixture of ionones and reactive aldehydes. Aldehydes react with amine odors (such as fish and cigarette odors). FIGS. 5-7 show one non-limiting example of such an odor removal mechanism. FIG. 5 shows the presence of butylamine (a fish odor) in the air. FIG. 6 shows the presence of Lilial (an aldehyde) in the air. FIG. 7 shows that when the two substances (the odorous butylamine and the malodor counteractant aldehyde-Lilial) are combined, the butylamine and lilial are no longer present in the air, and a new substance is formed without the odors that are characteristic of amines.

Liquid Mist Odor Traps

Another type of air freshening composition comprises liquid mist odor traps with built in water-soluble malodor counteractants. The liquid mist can remove malodors by taking them out of the air when the mist is suspended in the air and falls to the ground. Hydrophilic malodors (such as smoke, fish, onion, etc) dissolve in the mist in situ in the liquid phase. The non-volatile malodor counteractants (such as cyclodextrins, ionones, polyacrylic acid, etc) neutralize the malodor when the composition is a mist suspended in the air. Cyclodextrin forms complexes with different organic molecules to make them less volatile. Ionones react with amines. Polyacrylic acid neutralizes amines and thiols.

Figure 8:
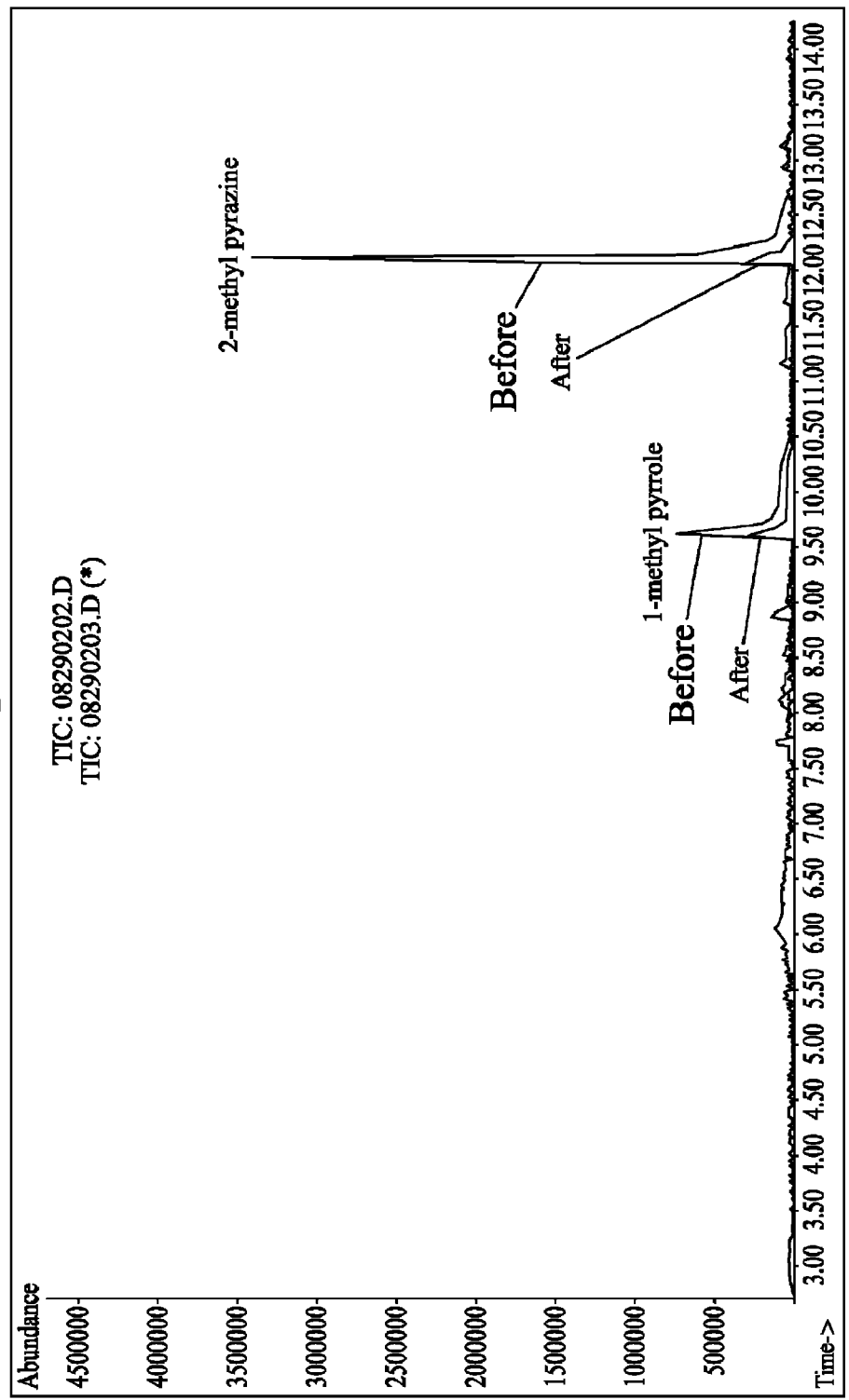
FIG. 8 is a graph that shows the concentration of two types of cigarette malodors in the air over time before and after a malodor counteractant is introduced into the air space.
Figure 9:
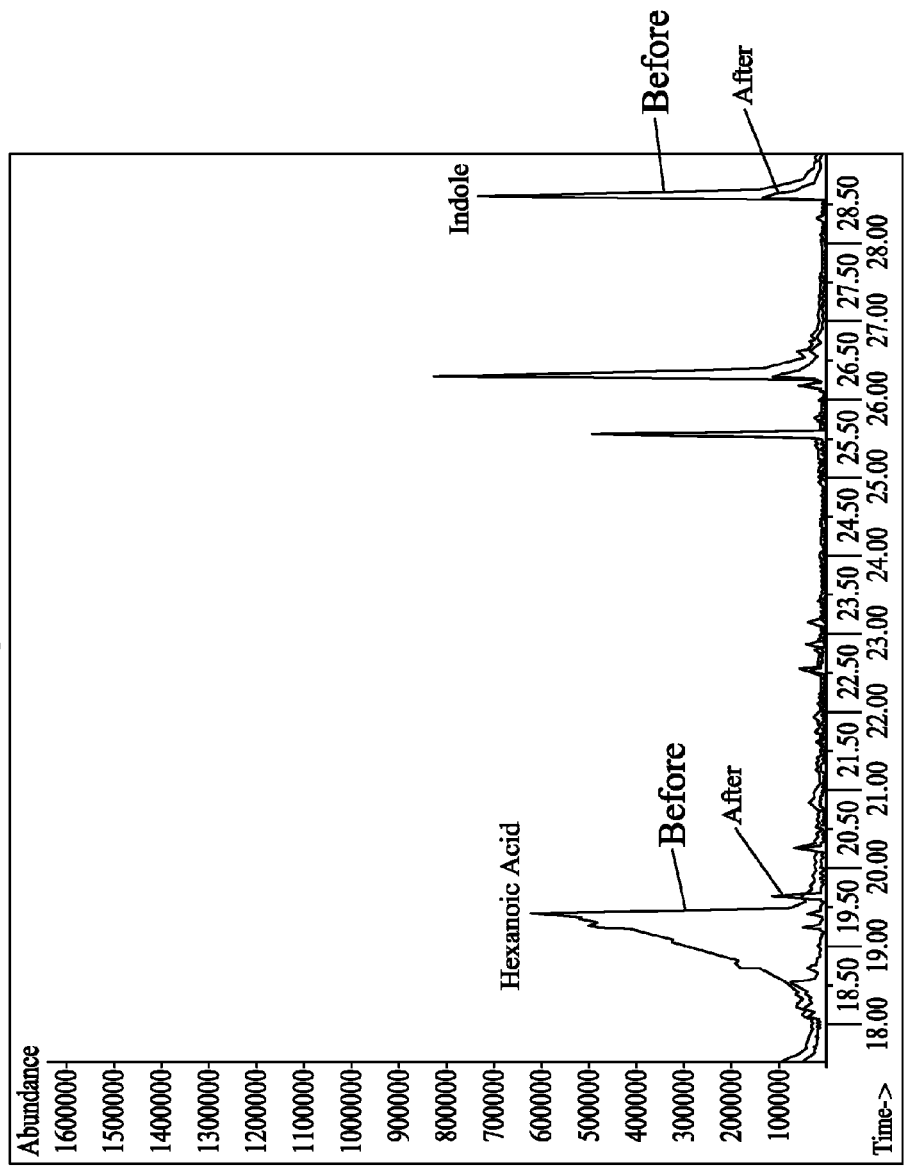
FIG. 9 is a graph that shows the concentration of body and bathroom malodors in the air over time before and after a malodor counteractant is introduced into the air space.

FIGS. 8 and 9 show the effect of liquid mist odor traps on some common types of odors. FIG. 8 shows the reduction in concentration of two types of cigarette malodors in the air before and after a malodor counteractant is introduced into the air space. FIG. 9 shows the reduction in concentration of body and bathroom malodors in the air before and after a malodor counteractant is introduced into the air space.

Sensory Modification

Other types of air freshening compositions function by sensory modification of those exposed to odors. There are at least two ways of modifying the sensory perception of odors.

One way (habituation) is to mask odors using perfume so that a person exposed to the odor smells the perfume more than the odor. The other way (anosmia) is to reduce the person's sensitivity to malodors. Ionones are compositions that are capable of reducing the sensitivity of a person's olfactory system to the presence of certain undesirable odors, such as sulfur odors caused by eggs, onions, garlic, and the like.

The air freshening composition can employ one or more of the types of malodor control mechanisms and ingredients described above (e.g., hydrophilic odor traps, vapor phase technology, and odor blockers (sensory modifiers).

The air freshening composition can be made in any suitable manner. All of the perfume ingredients and any malodor counteractant ingredients can simply be mixed together. In certain embodiments, it may be desirable to use the mixture of perfume and malodor counteractants as a concentrated product (and to dispense such a concentrated product, such as by spraying). In other embodiments, the mixture of ingredients can be diluted by adding the same to some suitable carrier and that composition can dispensed in a similar manner. Any suitable carrier can be used, including, but not limited to aqueous carriers, such as water and/or alcohols.

The perfume ingredients and any malodor counteractant ingredients can comprise any suitable percentage of the air freshening composition. The balance can be comprised of the carrier, and any optional ingredients. Optional ingredients include, but are not limited to: solvents, alcohols (e.g., etha-nol), surfactants, preservatives, and other quality control ingredients. In certain embodiments, the perfume ingredients and the malodor counteractant ingredients comprise from about 0.01% to about 100% of the air freshening composition, by weight, or any other range within this range. In embodiments in which the perfume and any malodor counteractant ingredients are diluted, one non-limiting example of such a narrower range is between about 0.05% and about 1% of the air freshening composition. In other embodiments, one or more fabric-safe aldehydes and/or or more fabric-safe ionones comprise less than or equal to about 25% of the weight of said composition.

| | Air Freshener Composition with Malodor Counteractant | | | | | |
|---|---|---|---|---|---|---|
| | Examples | | | | | |
| Ingredients | I Wt % | II Wt % | III Wt % | IV Wt % | V Wt % | VI Wt % |
| (A) Liquid Product | | | | | | |
| HPBCD[a] | 0.2 | — | — | — | 0.3 | 0.1 |
| Polyacrylic acid | 0.1 | 0.1 | 0.1 | — | 0.1 | 0.05 |
| Diethylene glycol | 0.25 | — | — | — | — | — |
| Silwet L-7600 | 0.1 | 0.1 | 0.1 | 0.1 | 0.1 | 0.1 |
| Sodium Dioctyl Sulfosuccinate | 0.2 | 0.1 | 0.2 | 0.1 | 0.2 | 0.2 |
| Ethanol | 3.0 | 5.0 | 5.0 | 3.0 | 5.0 | 5.0 |
| PEG60 Hydrogenated castor oil | 0.4 | 0.8 | 1.2 | 1.6 | 1.8 | 5.0 |
| Perfume | 0.6 | 0.8 | 0.4 | 0.2 | 1.0 | 0.1 |
| Proxel GXL | 0.015 | 0.015 | 0.015 | 0.015 | 0.015 | 0.015 |
| HCl or NaOH | to pH 5 | to pH 5 | to pH 5 | to pH 5 | to pH 7 | to pH 8.0 |
| Distilled water | Bal. | Bal. | Bal. | Bal. | Bal. | Bal. |
| Flow rate | 0.7 | 0.8 | 0.9 | 1.2 | 0.6 | 0.8 |
| (B) Propellant: Nitrogen preferred | | | | | | |

Ratio of Product to Propellant: 60/40 to 70/30 by volume.

[a]Hydroxypropyl beta-cyclodextrin.

Methods of Freshening Air

The methods of freshening air can comprise providing an air freshening composition that comprises a perfume composition, and optionally one or more malodor counteractants; and dispersing the air freshening composition into the air. The air freshening composition can be dispersed by any of the sprayers, articles and devices described herein, or by any other suitable device, or in any other suitable manner. The air freshening composition can be dispersed in the form of spray droplets, and in some cases, it may be desirable for the droplets to have the droplets sizes of the particular size specified herein. The method can be carried out in such a way to achieve any of the results that are specified herein. For example, in one non-limiting embodiment, the method can be carried out in a manner such that the perfume has an intensity measured on a sensory rating scale of 0-5 that is in a range of greater than or equal to about 2.5 but less than about 3.5 at the following times: (1) 2 minutes after the composition is first dispersed; and (2) 5 minutes after the composition is first disbursed.

Test Methods

Perfume Intensity Test

Odor Room Description—19 m³ in size, linoleum flooring, dry wall on walls, acoustic tile ceiling. Rooms also contain a toilet, sink, countertop and shower stall.

Perfume Intensity Evaluation Procedure

1. The odor room air controller is set for exhaust (which removes air from the room to outside the building) for fifteen minutes.

2. A trained odor evaluator verifies that there is not any residual perfume or room odor present in the room. The odor room air controller is set to the "off" position, which stops any air flow or air exchange within the room (note: Relative Humidity and temperature are not controlled and can vary depending on the time of year).
3. Trained odor evaluators enter the odor room and close the door.
4. An aerosolized air care sample is sprayed in the odor room for three seconds.
5. Trained odor evaluators perform perfume odor evaluations over the next sixty seconds, making observations on intensity, character and distribution within the room. All doors are closed upon exiting the room and remain closed during the test period.
6. The same trained odor evaluators re-enter the odor room, closing the door upon entry and perform perfume odor evaluations at 5 minutes and 30 minutes after the initial evaluation.

Perfume Intensity Scale:
5=very strong, i.e., extremely overpowering, permeates into nose, can almost taste it
4=strong, i.e., very room filling, but slightly overpowering
3=moderate, i.e., room filling, character clearly recognizable
2=weak, i.e., can be smelled in all corners, still can recognize character
1=very weak, i.e., cannot smell in all parts of the room
0=no odor Malodor Removal Test
Odor Room Description—640 ft³ in size, linoleum type flooring, dry wall on walls and ceiling.
Odor Evaluation Procedure
1. The odor room air controller is set for exhaust (which removes air from the room to outside the building) for a minimum of fifteen minutes.
2. A trained odor evaluator verifies that there is not any residual perfume, malodor contaminant or room odor present in the room. The odor room air controller is set to the "off" position, which stops any air flow or air exchange within the room (note: Relative Humidity and temperature are not controlled and can vary depending on the time of year).
3. A test facilitator introduces malodor into two rooms for malodor testing preparation.
4. Trained odor evaluators enter each room and perform odor evaluations over the next sixty seconds, making observations on malodor intensity, character and distribution within the room. All doors are closed upon exiting the room and remain closed during the test period.
5. A test facilitator sprays an aerosolized test product into only one of the rooms and the other room is maintained as a "malodor only" control.
6. Trained odor evaluators re-enter each room and perform odor evaluations over the next sixty seconds, making observations on intensity, character and distribution within the room. For the room that has been treated with the test product observations are made on both perfume odor and malodor reduction. All doors are closed upon exiting the room and remain closed during the test period.
7. The same trained odor evaluators re-enter each of the two odor rooms, closing the door upon entry and perform malodor and/or perfume odor evaluations at 5 minutes and 20 minutes after the initial evaluation.

Room Malodor Intensity Scale:
5=very strong, i.e., overpowering, permeates into nose, can almost taste it
4=strong, i.e., very room filling, but not overpowering
3=moderate, i.e., room filling, character clearly recognizable
2=weak, i.e., can be smelled in all corners, still can recognize character
1=very weak, i.e., cannot smell in all parts of the room
0=no odor The air freshening composition can, in certain embodiments, provide a reduction is malodors in any amount after any period of time including, but not limited to 5 minutes and 20 minutes after initial evaluation.

In both of the foregoing tests, it is possible to have intensities that are between (e.g., midway between) any of the numbers on the scale.

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

All percentages stated herein are by weight unless otherwise specified. It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

While particular embodiments of the subject invention have been described, it will be obvious to those skilled in the art that various changes and modifications of the subject invention can be made without departing from the spirit and scope of the invention. In addition, while the present invention has been described in connection with certain specific embodiments thereof, it is to be understood that this is by way of illustration and not by way of limitation and the scope of the invention is defined by the appended claims which should be construed as broadly as the prior art will permit.

What is claimed is:
1. A method of freshening air and improving a perfume release profile of an air freshening composition, comprising dispersing an air freshening composition into the air, wherein said air freshening composition comprises a perfume composition, and wherein said air freshening composition is provided in a container, said container comprising:
   a) a propellant comprising a compressed gas selected from the group consisting of compressed air, nitrogen, nitrous oxide, inert gases, and carbon dioxide, wherein said propellant is substantially free of hydrocarbons; and
   b) a dispenser;
   wherein the ratio of said compressed gas to said air freshening composition is 40:60 to 30:70 by volume, wherein, when said container is completely filled with said propellant and said air freshening composition, said air freshening composition is released from said container at a flow rate of from about 0.8 grams/second to about 1.5 grams/second, wherein the mean particle size of the released spray droplets is from about 10 microns to about 100 microns.

2. The method of claim 1 wherein said flow rate is from about 0.8 grams/second to about 1.2 grams/second.

3. The method of claim 1 wherein said flow rate is from about 0.8 grams/second to about 1.1 grams/second.

4. The method of claim 1 wherein said released spray droplets have a mean particle size of about 20 microns to about 60 microns.

5. The method of claim 1 wherein said container is a non bag-in-can container.

6. The method of claim 1 wherein the air freshening composition further comprises a malodor counteractant, and said perfume has an initial character as detected by a sensory panel prior to the inclusion of said malodor counteractant into said air freshening composition, and a character that is substantially the same after the inclusion of said malodor counteractant into said air freshening composition.

7. The method of claim 6 wherein said malodor counteractant comprises at least one of the following: cyclodextrin, carboxylic acids including mono, di, tri, and polyacrylic acids, and mixtures thereof.

8. The method of claim 6 wherein said malodor counteractant comprises a mixture of two or more of the following: (1) one or more fabric-safe aldehydes; (2) one or more fabric-safe ionones; and (3) at least one of the following: cyclodextrin, carboxylic acids including mono, di, tri, and polyacrylic acids, and mixtures thereof.

9. A method of freshening air and improving a perfume release profile of an air freshening composition, comprising dispersing an air freshening composition into the air, wherein said air freshening composition comprises a perfume composition, and wherein said air freshening composition is provided in a container holding at least about 120 grams of said air freshening composition, said container comprising:
   a) a propellant comprising a compressed gas selected from the group consisting of compressed air, nitrogen, nitrous oxide, inert gases, and carbon dioxide, wherein said propellant is substantially free of hydrocarbons; and
   b) a dispenser;
   wherein, when said container is completely filled with said propellant and said air freshening composition, said air freshening composition is released from said container at a flow rate of from about 0.8 grams/second to about 1.5 grams/second, wherein the mean particle size of the released spray droplets is from about 10 microns to about 100 microns.

10. The method of claim 9 wherein said container holds at least about 130 grams of said air freshening composition.

11. The method of claim 9 wherein said container holds at least about 150 grams of said air freshening composition.

12. The method of claim 9 wherein the ratio of said compressed gas to said air freshening composition is 40:60 to 30:70 by volume.

13. A method of freshening air and improving a perfume release profile of an air freshening composition, comprising dispersing an air freshening composition into the air, wherein said air freshening composition comprises a perfume composition comprising:
   a) at least about 1% by weight of said perfume composition of ingredients having a boiling point less than or equal to about 250° C. and Clog P value less than or equal to about 3,
   b) at least about 10% by weight of said perfume composition of ingredients having a boiling point less than or equal to about 250° C. and Clog P value greater than or equal to about 3,
   c) at least about 5% by weight of said perfume composition of ingredients having a boiling point greater than or equal to about 250° C. and Clog P value less than or equal to about 3,
   d) at least about 1% by weight of said perfume composition of ingredients having a boiling point greater than or equal to about 250° C. and Clog P value greater than or equal to about 3; and
   wherein said air freshening composition is provided in a container, said container comprising:
   e) a propellant comprising a compressed gas selected from the group consisting of compressed air, nitrogen, nitrous oxide, inert gases, and carbon dioxide, wherein said propellant is substantially free of hydrocarbons; and
   f) a dispenser;
   wherein the ratio of said compressed gas to said air freshening composition is 40:60 to 30:70 by volume, wherein said air freshening composition is released from said container at a flow rate of about 0.8 grams/second to about 1.5 grams/second, and wherein the mean particle size of the released air freshening composition is from about 10 microns to about 100 microns.

* * * * *